United States Patent [19]

Young et al.

[11] 4,010,167
[45] Mar. 1, 1977

[54] METHOD FOR THE RECOVERY OF ZEARALENONE

[75] Inventors: Vernon V. Young; John S. Kosewicz; Frederick William Schmitz, all of Terre Haute, Ind.

[73] Assignee: IMC Chemical Group, Inc., Terre Haute, Ind.

[22] Filed: Aug. 22, 1975

[21] Appl. No.: 606,957

[52] U.S. Cl. ........................................ 260/343.2 F
[51] Int. Cl.² ....................................... C07D 313/00
[58] Field of Search ............................. 260/343.2 F

[56] References Cited

UNITED STATES PATENTS 3,196,019  7/1965  Andrews et al. ............ 260/343.2 F
3,580,929  5/1971  Hidy et al. .................. 260/343.2 F

*Primary Examiner*—Anton H. Sutto
*Attorney, Agent, or Firm*—Morton, Bernard, Brown, Roberts & Sutherland

[57] ABSTRACT

Zearalenone is recovered from an aqueous mixture including zearalenone, water, and undissolved solids by a method comprising dissolving the zearalenone by contacting it with a zearalenone-dissolving mixture of water and a water-miscible, organic solvent, removing the undissolved solids, increasing the proportion of water to organic solvent to precipitate the zearalenone, and recovering the precipitated zearalenone.

35 Claims, No Drawings

METHOD FOR THE RECOVERY OF ZEARALENONE

The present invention generally relates to a method for recovering zearalenone from an aqueous mixture including an aqueous phase and a solid phase, containing, in the solid phase, zearalenone, and other undissolved solids. Zearalenone may be represented by the following chemical structural formula:

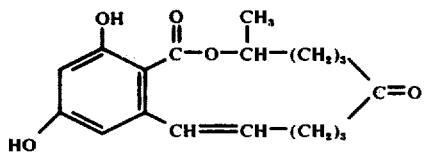

Zearalenone is a natural fermentation product which may be produced by the cultivation of a zearalenone-producing strain of the microorganism *Gibberella zeae* on a suitable aqueous nutrient medium.

Methods employed for the production of zearalenone by fermentation of *Gibberella zeae* in an aqueous nutrient medium are described, for instance, by Andrews, F. N. et al., U.S. Pat. No. 3,196,019 issued July 20, 1965, and Keith, C. L., U.S. Pat. No. 3,661,712 issued May 9, 1972, incorporated herein by reference.

The fermentation process described by Andrews et al. employs a solid, porous substrate for the nutrient medium. The fermentation process described by Keith includes submerged cultivation of a submergible zearalenone-producing culture of *Gibberella zeae* in a suitable, aerated, liquid phase nutrient medium, e.g. an aqueous solution of a carbohydrate source, an organic or inorganic nitrogen source, minerals, and other nutrients.

The fermented medium which contains zearalenone, water, and undissolved solids, such as *Gibberella zeae* mycelium, is often referred to as the fermentation beer. Zearalenone is substantially insoluble in the fermentation beer, and there is a need for a method for recovering zearalenone from a fermentation beer in high yields, and high purity.

In accordance with the invention, there is disclosed a method for recovering zearalenone from an aqueous mixture including an aqueous phase and a solid phase, containing, in the solid phase, zearalenone and other undissolved solids, which comprises:

a. contacting the zearalenone with a zearalenone-selective mixture consisting essentially of a water-miscible, organic solvent and water in amounts sufficient to selectively dissolve and transmit the zearalenone from the solid phase to the aqueous phase and provide a pumpable zearalenone solution;

b. removing the undissolved solids from the zearalenone solution at a temperature sufficiently high to maintain the zearalenone in solution and sufficiently low to avoid dissolving the solids, thereby forming a clarified zearalenone solution;

c. increasing the proportion of water-to-water-miscible, organic solvent in the clarified zearalenone solution to precipitate the zearalenone; and d. separating the precipitated zearalenone from its mother liquor at a temperature at which zearalenone is substantial insoluble in its mother liquor.

The method of the present invention is useful for recovering zearalenone from an aqueous mixture and is particularly advantageous for recovering zearalenone from a fermentation beer. The method may be employed for recovering zearalenone from a liquid fermentation beer resulting from a submerged fermentation, as described by Keith, C. L., supra, or from a solid, porous substrate such as described by Andrews, F. N. et al, supra.

In utilizing the method of this invention, the zearalenone is contacted with a zearalenone-selective mixture consisting essentially of a water-miscible, organic solvent and water (hereinafter sometimes referred to as an aqueous solvent mixture). The amount of the aqueous solvent mixture used is sufficient to selectively dissolve and transmit substantially all of the zearalenone from the solid phase to an aqueous phase, and will vary with the amount of water in the aqueous solvent mixture, the particular water miscible organic solvent used, the amount of zearalenone being recovered, the temperature, etc. The concentration of the water-miscible organic solvent in the aqueous solvent mixture varies with the particular solvent used. A reason for using a mixture of water and water-miscible, organic solvent, rather than a neat solvent is that a minimum amount of organic solvent is required to provide a slurry which may be conveniently and safely used in liquid handling equipment, i.e. a pumpable slurry.

To determine the minimum concentration of water-miscible, organic solvent which may be used in an aqueous solvent mixture, the total amount of liquid necessary to provide a slurry with the desired liquid consistency must be first ascertained. Based on this total amount of aqueous solvent mixture to be used, the ratio of water to water-miscible, organic solvent is such that the aqueous solvent mixture will dissolve the zearalenone present. Any water-miscible organic solvent may be used which provides a zearalenone-selective, aqueous solvent mixture, and advantageously they include oxygen-containing aliphatic compounds such as acetone, and alkanols of 1 to 4 carbon atoms, e.g. methanol, ethanol, propanol, and butanol. Acetone is preferred in the method of the present invention because of its solvent properties; however, methanol may be the commercially preferred water-miscible, organic solvent because it usually is significantly less costly than acetone, and also has a lower flash point than acetone, thereby providing safety benefits.

The volume of aqueous solvent mixture which can be used has generally been found to be an amount sufficient to provide slurries of from about 10% to about 60% by wt. solids, preferably about 30–50% by wt. solids. Such slurries are generally pumpable liquids which may be used in liquid handling equipment. A liquid fermentation beer resulting from a submerged fermentation, generally has an adequate liquid consistency for use in liquid handling equipment, thus the aqueous solvent mixture may be formed in situ by adding enough water-miscible organic solvent to the fermentation beer to render the zearalenone therein soluble.

It may be desirable to separate the solids from such a liquid fermentation beer prior to contacting the zearalenone with the zearalenone-selective mixture, e.g. by filtration or centrifugation. The separation may be effected to remove dissolved impurities prior to recovery, and to allow the use of smaller volumes of aqueous solvent mixture for the recovery. When such a separation is employed, the solids (hereinafter sometimes called the filter cake), which contain the zearalenone, are slurried with the aqueous solvent mixture. The volume of aqueous solvent mixture used is sufficient to provide a substantially liquid slurry having a solids content as hereinbefore described, and advantageously is about equal to the volume of fermentation beer from which the solids were obtained. When the method of this invention is utilized for the recovery of zearalenone from a solid porous substrate, the dissolution of the zearalenone may be conducted in the same manner as the recovery from a filter cake from a liquid fermentation beer.

The preferred aqueous solvent mixture is about 40% to 60% by vol. acetone; however, aqueous acetone containing from about 25% by vol. acetone functions satisfactorily. Aqueous methanol and ethanol are most effective at concentrations of about 50% to 75% by vol.; however, ranges from about 40% of alcohol by vol. are effective, for instance, about 40 to about 75% by vol. methanol may be employed. Propanol and butanol are effective at concentrations of at least about 75% by vol., preferably at least about 90% by vol.

The zearalenone in the aqueous mixture is contacted with the aqueous solvent mixture for a time sufficient to selectively dissolve substantially all of the zearalenone present, thereby forming a zearalenone solution. The time period required will depend on the particular aqueous solvent mixture used and the temperature of the aqueous solvent mixture, etc., but generally about 10 minutes to about five hours, preferably about 30 minutes to about 2 hours will be sufficient to dissolve the zearalenone. After the zearalenone has been dissolved, the undissolved solids are removed from the zearalenone solution, e.g., by filtration or centrifugation, leaving a clarified zearalenone solution. The temperature of the solvent during the separation is advantageously high enough to maintain the zearalenone in solution and sufficiently low to avoid dissolving other solids. Generally about room temperature or less to elevated temperatures substantially below the boiling point of the water-miscible organic solvent provides satisfactory results, e.g. about 10° C to about 60° C, preferably about 20° C to about 40° C. The spent solids may be discarded or re-extracted to remove any remaining zearalenone present.

The zearalenone in the clarified zearalenone solution is precipitated, preferably in quantitative amount, by increasing the proportion of water to water-miscible, organic solvent. This increase may advantageously be accomplished by removing substantially all of the water-miscible, organic solvent from the clarified zearalenone solution by any suitable means such as evaporation under a stream of air, or distillation at atmospheric or reduced pressure. Distillation at a reduced pressure, preferably approximately 200 mm. Hg or less, is the preferred method of removing the water-miscible, organic solvent. When this method of solvent removal is employed, the absence of solvent may be determined by monitoring the temperature at the top of the distillation column. A temperature rise to approximately the boiling point of water at the pressure employed indicates that substantially all of the solvent has been removed.

Another method of increasing the proportion of water to water-miscible, organic solvent in the clarified zearalenone solution is by adding water. The water is added until zearalenone ceases to precipitate with the addition of more water. A simple method to determine when sufficient water has been added is as follows:

A small aliquot of the mixture is filtered into a test tube. If zearalenone does not precipitate when water is added to the test tube, essentially quantitative precipitation has been obtained.

After precipitation, the zearalenone is separated from its mother liquor by any suitable means such as filtration or centrifugation. During separation, the temperature of the mixture is maintained at a level such that the zearalenone is substantially insoluble in its mother liquor. Generally, a temperature range of about 0° C to about 40° C has been found to be satisfactory. The preferred temperature range is from about 15° C to about 25° C. The resulting zearalenone crystals may be washed with water and dried.

The recovery method of this invention provides yields of approximately 80% and product purities of about 85% to 95%. A further advantage of the method of this invention is that filtering of zearalenone-containing slurries, such as liquid fermentation beers, is much facilitated by the addition of a water-miscible, organic solvent. Little or no filter-aid is usually required, thus simplifying recovery, and providing improved yields. The application of this invention provides an efficient recovery method in which minimal amounts of organic solvent are required, liquid handling equipment may be conveniently utilized, and safer conditions, as compared to the use of substantially pure organic solvents, are realized.

The following examples illustrate the method of the present invention, but the examples are not intended to limit the invention.

EXAMPLE I

A zearalenone-containing, fermentation beer was prepared as follows. A stage A fermentation was started in 100 ml. of Bennett's broth in a 500 ml. Erlenmeyer flask with a 5 ml. aliquot of a mycelial suspension of a submergible, zearalenone-producing strain of *Gibberella zeae*. The Bennett's broth had the following composition:

| | |
|---|---|
| Glucose | 10 g/l |
| NZ Amine Type A | 2 g/l |
| Yeast Extract | 1 g/l |
| Beef Extract | 1 g/l |
| Sodium Chloride | 2.5 g/l |
| H₂O to volume | |

NZ Amine Type A is a pancreatic hydrolyzate of casein which contains, in the form of mixed amino acids and peptides, all amino acids originally present in casein. It is purchased from Sheffield Chemical Division of National Dairy Products, Norwich, New York.

The flask was incubated at 30° C on a rotary shaker for 20–24 hours.

Each of six stage B flasks was started with five milliliters of the stage A mixture and 100 ml. of the Bennett's broth. The same fermentation conditions were used as in the stage A fermentation.

Each of six stage C flasks containing 2 liters of Bennett's broth in a 6 liter Erlenmeyer flask equipped with a side arm and inoculum transfer hose was inoculated with the entire contents of a stage B flask. The mixture was incubated for 24 hours at 30° C on a reciprocal shaker.

Fifty gallons of Bennett's broth was prepared in each of two 100 gallon seed fermentors for the final inoculum stage. These fermentors were each inoculated with three stage C flasks. The mixtures were incubated for 24 hours at 28°–30° C. Agitation and aeration of each mixture was accomplished by maintaining an air flow through a circular sparger of about 5–7 cubic feet per minute.

The contents of both seed fermentors were used to inoculate 1350 gallons of production medium (total volume 1450 gal). The production medium had the following composition:

| | |
|---|---|
| Glucose | 330 g/l |
| Lard oil | 600 ml |
| Potassium chloride | 0.25 g/l |
| Magnesium sulfate . 7H$_2$O | 0.25 g/l |
| Potassium phosphate dibasic anhydrous | 0.50 g/l |
| Urea | 4.10 g/l |
| NZ-Amine Type A (Sheffield) | 3.00 g/l |
| Zinc sulfate . 7H$_2$O | 1.0 p.p.m. |
| Distilled water to volume | |

The medium was autoclaved at 121° C for 14 minutes and pumped rapidly into a pre-chilled cooling vessel. The mixture was then inoculated with the contents of the seed fermentors and incubated at 21–22° C for about 21 days. The medium was aerated with air through a circular sparger at 180 cubic feet per minute. Agitation was accomplished by a three-turbine rotor at a rate of 105 rpm.

To each of eight 500 ml. portions of the fermentation beer was added 5 grams of filter aid and five hundred milliliters of acetone. The mixture was stirred for 30 minutes then vacuum filtered. The filter cake was washed with 100 ml. of 50% aqueous acetone. The filtrate and wash solutions were combined, stirred, and the acetone removed by evaporation at room temperature under a stream of dry air. The precipitated zearalenone was collected on a coarse, sintered glass filter, rinsed with water, and dried.

In each of the eight runs one or more of the fermentation beer, filter, cake, filtrate, and recovered zearalenone were assayed for zearalenone content by known methods. The results of the assays are reported in Table I.

TABLE I

| Run | Fermentation Beer Zearalenone Assay, g/l | Filter Cake Wt., g(1) | Filter Cake Z. Assay, Wt.% | Filtrate Vol., ml | Filtrate Z. Assay, g/l | Pptd. Zearalenone Wt., g | Pptd. Zearalenone Pur. %(Wt.) | Pptd. Zearalenone Rec. %(Wt.) |
|---|---|---|---|---|---|---|---|---|
| 1 | 8.1 | 43.5 | 0.35 | 510 | Nil | 4.25 | 94.9 | 99.5 |
| 2 | 8.1 | 44.1 | 0.06 | 514 | Nil | 4.50 | 90.6 | Quan. |
| 3 | 14.5 | 46.8 | 0.00 | 513 | Nil | 8.23 | 97.7(2) | Quan. |
| 4 | 14.5 | 46.7 | 0.21 | 509 | Nil | 7.60 | 94.5 | 98.0 |
| 5 | 11.6 | — | — | — | — | 6.10 | 90.3 | 95.0 |
| 6 | 11.6 | — | — | — | — | 6.25 | 91.0 | 98.0 |
| 7 | 17.0 | — | — | — | — | 9.45 | 92.4 | Quan. |
| 8 | 17.0 | — | — | — | — | 9.30 | 92.2 | Quan. |

(1)Mycelium wt. approximately 10–15 g.
(2)Purity assay may be high.

EXAMPLE II

In each of six runs, 1500 ml of fermentation beer which was prepared by the method described in Example I had added to it 1500 ml of acetone. Char was then added to the mixture as indicated in Table II. The mixture was stirred for one-half hour, filtered, and the filter cake was rinsed with 300 ml of 50% aqueous acetone. The filtrate and rinse solutions were combined and the acetone was removed as follows:

An acetone stripper consisted of a 2-liter resin pot equipped with an agitator, dropping funnel, thermometer, condenser and vacuum controls. The resin pot was charged with 200 ml of water, heated to approximately 60° C, and the acetone filtrate was added slowly over a four hour period. The process was terminated when the pot temperature rose to 70° C at 200 mm Hg. The residual water-zearalenone slurry was cooled to 20° C, and filtered using a coarse, sintered glass funnel. The zearalenone crystals were washed with water and dried.

The zearalenone levels were determined analytically in the fermentation beer, the filter cake, the filtrate and in the recovered zearalenone. The results are reported in Table II.

TABLE II

| Run | Fermentation Beer Z. Assay, g/l | Char, g | Precipitated Zearalenone Wt., g | Precipitated Zearalenone Pur. %(Wt.) | Precipitated Zearalenone Recovery %(Wt.) |
|---|---|---|---|---|---|
| 1 | 17.0 | None | 27.30 | 91.0 | 97.4 |
| 2 | 17.0 | 20.0 | 26.80 | 91.4 | 96.1 |
| 3 | 13.3 | 15.0 | 20.80 | 94.6 | 98.4 |
| 4 | 13.3 | 15.0 | 20.35 | 94.7 | 96.5 |
| 5 | 13.6 | 15.0 | 21.00 | 92.2 | 94.4 |
| 6 | 13.6 | 15.0 | 20.70 | 94.0 | 95.3 |

EXAMPLE III

The experiment of Example II is repeated in all essential details except that 4500 ml. of methanol is substituted for 1500 ml. of acetone. Zearalenone is recovered in satisfactory yield.

EXAMPLE IV

The experiment of Example II is repeated in all essential details except that 4500 ml. of ethanol is substituted for 1500 ml. of acetone. Zearalenone is recovered in satisfactory yield.

EXAMPLE V

A zearalenone-containing fermentation beer (1500 ml.) prepared as described in Example I was filtered. The filter cake was slurried at room temperature with 3000 ml. of 50% by vol. of acetone in water for a period of about one hour. The slurry was then filtered, and the resulting solids were washed with 300 ml. of 50% by vol. acetone in water. The filtrate was transferred to a vacuum distillation apparatus and was slowly distilled at about 200 mm. Hg pressure until the temperature at the top of the distillation column reached 67° C. The filtrate was then cooled to about 20° C and the precipitated zearalenone was removed by filtration. The zearalenone crystals were washed with water and dried. The process yielded 87.5% by wt. recovery (based on 100% product) of material containing about 94% by wt. zearalenone.

EXAMPLE VI

A zearalenone-containing fermentation beer (1500 ml.) prepared as described in Example I was filtered. The filter cake was slurried at room temperature with 1500 ml. of methanol for a period of about one hour. The slurry was then filtered, and the resulting solids were washed with 300 ml. of methanol. The filtrate was transferred to a vacuum distillation apparatus and diluted with about 600 ml. of water. The mixture was distilled at about 200 mm. Hg pressure until the temperature at the top of the distillation column reached about 60° C. The filtrate was then cooled to about 20° C and the precipitated zearalenone crystals were washed with water and dried. The process yields about 98% by wt. recovery (based on 100% product) of material containing about 94% by wt. zearalenone.

EXAMPLE VII

About 13 lb. of diatomaceous earth filter aid was added to 156 gallons of a zearalenone-containing fermentation beer which was prepared as described in Example I, and the mixture was filtered. The resulting filter cake was slurried with about 146 gallons of a 72% by vol. mixture of acetone in water for about one hour. The slurry was filtered, and the filtrate was transferred to an evaporator. The solution was distilled at about 100 mm. Hg pressure until the temperature reached about 53° C. The solution was then cooled to about 30°–35° C and filtered. The filtrate was returned to the evaporator and distilled again to a temperature of 55° C and filtered. The recovered zearalenone crystals were combined and dried. The process yielded about 84% by wt. recovery (based on 100% product) of material containing about 85% by wt. zearalenone.

EXAMPLE VIII

The experiment of Example VI is repeated in all essential details, except ethanol is substituted for methanol. Zearalenone is recovered in acceptable yield and product purity.

EXAMPLE IX

The experiment of Example VI is repeated in all essential details, except 2-propanol is substituted for methanol. Zearalenone is recovered in acceptable yield and product purity.

EXAMPLE X

The experiment of Example V is repeated in all essential details, except a 70% by vol. mixture of methanol in water is substituted for the 50% by vol. mixture of acetone in water. Zearalenone is recovered in acceptable yield and product purity.

EXAMPLE XI

A solid fermentation substrate is prepared as described in Example II of U.S. Pat. No. 3,196,019 issued to Andrews. One hundred grams of the fermented substrate is slurried into 200 ml. of a 60% by vol. aqueous acetone solution. The slurry is filtered at room temperature and the filter cake is washed with an additional 50 ml. of 50% by vol. aqueous acetone. The filtrate and wash solutions are combined and transferred to a distillation apparatus. The solution is distilled at 200 mm. Hg until the temperature at the top of the distillation column reaches 67° C. The distilled solution is then cooled to about 20° C and the precipitated zearalenone is recovered in satisfactory yield and purity.

We claim:
1. A method for recovering zearalenone from an aqueous mixture including an aqueous phase and a solid phase, containing, in the solid phase, zearalenone and other undissolved solids, which comprises:
   a. contacting the zearalenone with a zearalenone-selective aqueous solvent mixture consisting essentially of a water-miscible, organic solvent and water in amounts sufficient to selectively dissolve and transmit the zearalenone from the solid phase to the aqueous solvent phase and provide a pumpable zearalenone solution;
   b. removing the undissolved solids from the zearalenone solution at a temperature sufficiently high to maintain the zearalenone in solution and sufficiently low to avoid dissolving the solids, thereby forming a clarified zearalenone solution;
   c. increasing the proportion of water-to-water miscible, organic solvent in the clarified zearalenone solution to precipitate the zearalenone; and
   d. separating the precipitated zearalenone from its mother liquor at a temperature at which zearalenone is substantially insoluble in its mother liquor.
2. The method of claim 1 wherein the water-miscible, organic solvent is selected from the group consisting of acetone, methanol, ethanol, propanol, and butanol.
3. The method of claim 1 wherein the water-miscible, organic solvent is acetone.
4. The method of claim 1 wherein the water-miscible, organic solvent is methanol.
5. The method of claim 3 wherein the mixture of water and acetone contains acetone at a concentration of from about 40% to about 60% by vol.
6. The method of claim 4 wherein the mixture of water and methanol contains methanol at a concentration of from about 40% to about 75% by vol.
7. The method of claim 4 wherein the mixture of water and methanol contains methanol at a concentration of from about 50% to about 75% by vol.
8. The method of claim 1 wherein the temperature at which the undissolved solids are removed from the zearalenone solution is from about 10° C to about 60° C, and the temperature at which the precipitated zearalenone is separated from its mother liquor is from about 0° C to about 40° C.
9. The method of claim 1 wherein the temperature at which the undissolved solids are removed from the zearalenone solution is from about 20° C to about 40° C, and the temperature at which the precipitated zearalenone is separated from its mother liquor is from about 15° C to about 25° C.
10. The method of claim 1 wherein the proportion of water-to-water-miscible, organic solvent in the clarified zearalenone solution is increased by distilling off the water-miscible, organic solvent until the zearalenone has been substantially quantitatively precipitated.

11. The method of claim 1 wherein the proportion of water-to-water-miscible, organic solvent in the clarified zearalenone solution is increased by adding water until the zearalenone has been substantially quantitatively precipitated.

12. The method of claim 1 wherein the aqueous mixture including an aqueous phase and a solid phase is an aqueous, liquid, zearalenone-containing, fermentation beer resulting from the submerged cultivation of a zearalenone-producing strain of the microorganism *Gibberella zeae* in a nutrient medium; and the zearalenone in said fermentation beer is dissolved by adding a water-miscible, organic solvent to the beer to form a zearalenone-dissolving mixture of water and a water-miscible, organic solvent.

13. The method of claim 12 wherein the water-miscible, organic solvent is selected from the group consisting of acetone, methanol, ethanol, propanol, and butanol.

14. The method of claim 12 wherein the water-miscible, organic solvent is acetone.

15. The method of claim 12 wherein the water-miscible, organic solvent is methanol.

16. The method of claim 14 wherein the mixture of water and acetone contains acetone at a concentration of from about 40% to about 60% by vol.

17. The method of claim 15 wherein the mixture of water and methanol contains methanol at a concentration of from about 40% to about 75% by vol.

18. The method of claim 15 wherein the mixture of water and methanol contains methanol at a concentration of from about 50% to about 75% by vol.

19. The method of claim 12 wherein the temperature at which the undissolved solids are removed from the zearalenone solution is from about 10° C to about 60° C, and the temperature at which the precipitated zearalenone is separated from its mother liquor is from about 0° C to about 40° C.

20. The method of claim 12 wherein the temperature at which the undissolved solids are removed from the zearalenone solution is from about 20° C to about 40° C, and the temperature at which the precipitated zearalenone is separated from its mother liquor is from about 15° C to about 25° C.

21. The method of claim 12 wherein the proportion of water-to-water-miscible, organic solvent in the clarified zearalenone solution is increased by distilling off the water-miscible, organic solvent until the zearalenone has been substantially quantitatively precipitated.

22. The method of claim 12 wherein the proportion of water-to-water-miscible, organic solvent in the clarified zearalenone solution is increased by adding water until the zearalenone has been substantially quantitatively precipitated.

23. A method for recovering zearalenone from an aqueous, liquid, zearalenone-containing fermentation beer resulting from the submerged cultivation of a zearalenone-producing strain of the microorganism *Gibberella zeae* in a nutrient medium, comprising the steps of:

a. separating the solids from the fermentation beer, thereby forming a zearalenone-containing filter cake;

b. slurrying the zearalenone-containing filter cake with a zearalenone-dissolving mixture of water and a water-miscible, organic solvent, thereby forming a zearalenone solution;

c. removing the undissolved solids from the zearalenone solution at a zearalenone-dissolving temperature, thereby forming a clarified zearalenone solution;

d. increasing the proportion of water-to-water-miscible, organic solvent in the clarified zearalenone solution to precipitate the zearalenone; and e. separating the precipitated zearalenone from its mother liquor at a temperature at which zearalenone is substantially insoluble in its mother liquor.

24. The method of claim 23 wherein the water-miscible, organic solvent is selected from the group consisting of acetone, methanol, ethanol, propanol, and butanol.

25. The method of claim 23 wherein the water-miscible, organic solvent is acetone.

26. The method of claim 23 wherein the water-miscible, organic solvent is methanol.

27. The method of claim 25 wherein the mixture of water and acetone contains acetone at a concentration of from about 40% to about 60% by vol.

28. The method of claim 26 wherein the mixture of water and methanol contains methanol at a concentration of from about 40% to about 75% by vol.

29. The method of claim 26 wherein the mixture of water and methanol contains methanol at a concentration of from about 50% to about 75% by vol.

30. The method of claim 23 wherein the temperature at which the undissolved solids are removed from the zearalenone solution is from about 10° C to about 60° C, and the temperature at which the precipitated zearalenone is separated from its mother liquor is from about 0° C to about 40° C.

31. The method of claim 23 wherein the temperature at which the undissolved solids are removed from the zearalenone solution is from about 20° C to about 40° C, and the temperature at which the precipitated zearalenone is separated from its mother liquor is from about 15° C to about 25° C.

32. The method of claim 23 wherein the proportion of water-to-water-miscible, organic solvent in the clarified zearalenone solution is increased by distilling off the water-miscible, organic solvent until the zearalenone has been substantially quantitatively precipitated.

33. The method of claim 23 wherein the proportion of water-to-water-miscible, organic solvent in the clarified zearalenone solution is increased by adding water until the zearalenone has been substantially quantitatively precipitated.

34. The method of claim 1 wherein the aqueous mixture including an aqueous phase and a solid phase is a zearalenone-containing solid, porous substrate resulting from the cultivation of a zearalenone-producing strain of the microorganism *Gibberella zeae* on a solid, porous nutrient medium, and the zearalenone in said substrate is dissolved by slurrying it with a zearalenone-dissolving mixture of water and a water-miscible, organic solvent, thereby forming the zearalenone solution.

35. A method for recovering zearalenone from a solid phase containing a mixture of zearalenone and other solids, which comprises contacting the solid phase with a zearalenone-selective aqueous solvent mixture consisting essentially of a water-miscible, organic solvent and water in amounts sufficient to selectively dissolve the zearalenone and provide a pumpable zearalenone solution; removing undissolved solids from the zearalenone solution at a temperature sufficiently high to maintain the zearalenone in solution and sufficiently low to avoid dissolving the solids, thereby forming a clarified zearalenone solution; increasing the proportion of water-to-water-miscible, organic solvent in the clarified zearalenone solution to precipitate the zearalenone; and separating the precipitated zearalenone from its mother liquor at a temperature at which zearalenone is substantially insoluble in its mother liquor.

* * * * *